(12) United States Patent
Majeti et al.

(10) Patent No.: US 7,163,674 B2
(45) Date of Patent: *Jan. 16, 2007

(54) PERSONAL CARE COMPOSITIONS COMPRISING A DICARBOXY FUNCTIONALIZED POLYORGANOSILOXANE

(75) Inventors: Satyanarayana Majeti, Middletown, OH (US); Elizabeth Ann Brown Reno, Fairfield, OH (US); Stephen Andras Kovacs, Loveland, OH (US); Philippe Olier, Lyons (FR)

(73) Assignee: The Procter & Gamble Company, Cincinnati, OH (US)

( * ) Notice: Subject to any disclaimer, the term of this patent is extended or adjusted under 35 U.S.C. 154(b) by 111 days.

This patent is subject to a terminal disclaimer.

(21) Appl. No.: 10/430,647

(22) Filed: May 6, 2003

(65) Prior Publication Data

US 2003/0211057 A1    Nov. 13, 2003

Related U.S. Application Data

(60) Provisional application No. 60/378,992, filed on May 9, 2002.

(51) Int. Cl.
*A61K 8/00* (2006.01)

(52) U.S. Cl. .................. 424/70.1; 424/70.12; 424/424; 424/401; 528/25; 528/26; 528/31

(58) Field of Classification Search ................... 528/26, 528/31; 524/588; 424/70.12, 59, 64, 65, 424/401

See application file for complete search history.

(56) References Cited

U.S. PATENT DOCUMENTS

| | | | |
|---|---|---|---|
| 4,658,049 A | 4/1987 | Nakano et al. | |
| 4,876,152 A | 10/1989 | Kang | |
| 5,063,052 A * | 11/1991 | Grollier et al. | 424/70.121 |
| 5,087,443 A | 2/1992 | Chizat et al. | |
| 5,516,869 A | 5/1996 | Lucarelli et al. | |
| 5,702,490 A | 12/1997 | Kneip et al. | |
| 6,007,801 A | 12/1999 | Hossel et al. | |
| 2002/0028899 A1 | 3/2002 | Breunig et al. | |
| 2003/0212231 A1 * | 11/2003 | Olier | 528/10 |

FOREIGN PATENT DOCUMENTS

| | | |
|---|---|---|
| DE | 197 07 970 A1 | 3/1998 |
| EP | 196 169 | 4/1986 |
| JP | 02-164437 | 6/1990 |
| JP | 11-322943 | 11/1999 |

* cited by examiner

*Primary Examiner*—Marc S. Zimmer
(74) *Attorney, Agent, or Firm*—Bridget Murray; Emelyn L. Hiland

(57) ABSTRACT

Disclosed are personal care or cosmetic compositions comprising a dicarboxy functionalized polyorganosiloxane and methods for the cleaning or the treatment of hair or skin and for enhancing delivery of active agents to hair or skin with the compositions. Said personal care or cosmetic compositions can be formulated in a wide variety of types of products for the skin and/or hair (or, more generally, keratin) such as mousses, gels (in particular hair dressing gels), conditioners, hair dressing formulations or to aid comb-through of hair, rinsing formulae, hand and body lotions, skin moisturizing products, skin cleansing or disinfecting compositions, shower gels, toilet milks, cream foundations, make-up removal compositions, sun and ultraviolet radiation protection lotions, creams or gels, skin care creams, anti-age preparations, anti-acne preparations, local analgesics, mascaras, deodorants, antiperspirants, lipsticks and other compositions of the same type. The use of dicarboxy functionalized polyorganosiloxanes permits to confer benefits such as an increase in shine, gloss or volume of hair, easier comb-through of hair, easier spreadability or slipperiness onto skin; it also permits a better persistence of active materials or benefits agents deposited onto the surface and consequently permits to maintain the activity of the composition deposited on the surface over time. The dicarboxy functionalized polyorganosiloxane can be used in an amount of from about 0.1% to about 30%, preferably from about 3% to about 10% by weight, of said personal care or cosmetic compositions.

5 Claims, No Drawings

PERSONAL CARE COMPOSITIONS COMPRISING A DICARBOXY FUNCTIONALIZED POLYORGANOSILOXANE

CROSS REFERENCE TO RELATED APPLICATIONS

This application claims the benefit of U.S. Provisional Application No. 60/378,992, filed May 9, 2002.

FIELD OF THE INVENTION

The invention relates to personal care or cosmetic compositions comprising a dicarboxy functionalized polyorganosiloxane, for the cleaning or the treatment of hair or skin.

BACKGROUND OF THE INVENTION

Organofunctional silicones are well-known in the art. The siloxane units may be functionalized with substituents such as carboxyalkyl (EP-A-196 169; U.S. Pat. No. 5,702,490), carboxyalkylaminoalkyl (U.S. Pat. No. 5,516,869), carboxyetheralkyl (U.S. Pat. No. 4,658,049), with radicals derived from alkenyl succinic anhydride (U.S. Pat. No. 4,876,152) optionally amidated (U.S. Pat. No. 6,007,801) and can be used for the treatment of surfaces in various type of industries, such as metal, leather, personal care, plastics, and masonry.

It has now been found that particular dicarboxy functionalized polyorganosiloxanes are useful in personal care or cosmetic compositions for the treatment of hair or skin, targeted at conferring on the latter benefits such as gloss, shine, conditioning, spreadability, slipperiness, color care and/or at improving the residuality, impact and/or efficacy of active materials or benefits agents comprised in said formulations on the surface treated therewith.

DETAILED DESCRIPTION OF THE INVENTION

While the specification concludes with claims, which particularly point out and distinctly claim the invention, it is believed the present invention will be better understood from the following description.

All percentages and ratios used herein are by weight of the total composition unless otherwise specified. All measurements are made at 25° C., unless otherwise specified.

Herein, "comprising" means that other steps and other ingredients which do not affect the end result can be added. This term encompasses the terms "consisting of" and "consisting essentially of".

The personal care compositions for the cleaning or the treatment of hair and/or skin comprises at least one dicarboxy functionalized polyorganosiloxane of formula (I)

$$X(R^4R^5SiO)p(R^6ASiO)qY \quad (I)$$

wherein
the X end group represents a triorganosiloxyl end group of formula $R^1R^2R^3SiO-$, or a Z end group wherein Z represents $-OH$;
the Y end group represents a triorganosilyl end group of formula $-SiR^3R^2R^1$ or a W end group wherein W represents $-H$;
$R^1$ to $R^6$, which may be identical or different, each represents a linear or branched C1–C8 alkyl or phenyl radical, preferably methyl;

A represents a dicarboxy acid radical of formula

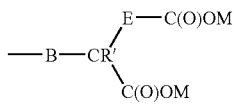

wherein
B represents an alkylene residue having from 2 to 30 carbon atoms, preferably from 3 to 8 carbon atoms, optionally substituted by one or more alkyl radicals having from 1 to 30 carbon atoms,
R' represents a hydrogen atom or an alkyl radical having from 1 to 30 carbon atoms, and
E is nil or is an alkylene residue having from 1 to 5 carbon atoms, preferably from 1 to 3 carbon atoms, optionally substituted by one or more alkyl radicals having from 1 to 30 carbon atoms; and
M is H or a cation or an alkyl radical having from 1 to 4 carbon atoms optionally substituted with hydroxy or alkoxy groups;
p is an average value ranging from 0 to 1000, preferably from 0 to 500, more preferably from 5 to 200; and
q is an average value ranging from 1 to 100, preferably from 1 to 50.

The ratio of the number of Z and W end groups to the total number of end groups X and Y ranges from 0/100 to 75/100, preferably from 0/100 to 30/100. The products where Z is —OH and/or Y is —H, are by-products.

The cation salts of the dicarboxy radical can be alkali metal (sodium, potassium, lithium) salts, alkaline earth metal (calcium, barium) salts, non substituted or substituted ammonium (methyl-, dimethyl-, trimethyl-, or tetramethylammonium, dimethylpiperidinium) salts or can derive from an alkanolamine (monoethanolamine, diethanolamine, triethanolamine).

In a preferred embodiment, the p/q ratio is from 1/3 to 99/1 (corresponding to 1–75% of pendant diacid groups relative to the siloxyl units), preferably from 1/1 to 10/1.

In addition to the mono- or diester derivatives of the dicarboxy radical (M=alkyl), the present invention includes the amide and diamide derivatives.

The present dicarboxy functionalized siloxane polymers are generally prepared by a hydrosilylation reaction of a polyalkylhydrogensiloxane and an alpha-olefinic anhydride, the precursor of the dicarboxy A groups, with the aid of an effective amount of a hydrosilylation metal catalyst (platinum), as described for example, in U.S. Pat. Nos. 3,159,601; 3,159,662; and 3,814,730, followed by hydrolysis of the anhydride groups.

The hydrosilylation reaction can be carried out at a temperature from 20 to 200° C., preferably from 60 to 120° C., preferably with the aid of a platinum KARSTEDT catalyst (from 1 to 300 ppm, preferably from 5 to 50 ppm by weight of Pt). The relative quantities of polyalkylhydrogensiloxane and alpha alkenyl anhydride corresponds to a stoichiometric excess of alpha alkenyl anhydride (at most 5 moles of alpha alkenyl anhydride per mole of polyalkylhydrogensiloxane, preferably at most 2 moles of alpha alkenyl anhydride per mole of polyalkylhydrogensiloxane.

The hydrolysis reaction can be carried out with water at a temperature ranging from room temperature to 150° C., preferably from 40 to 120° C., with or without catalysts. Suitable catalysts for the reaction can be Lewis acids such as $TiCl_4$, $ZnCl_2$, $MgCl_2$, or Bronstedt acids or bases such as $CH_3COOH$, $H_2SO_4$, HCl, KOH, $NaHCO_3$, in an amount ranging from 0.05 to 5%.

Preferred polymers comprise one or a combination of the following dicarboxy acid pendant groups:

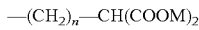

where n is from 2 to 30.

In a preferred embodiment, the diacid pendant group A in the functionalized polyorganosiloxane is $-(CH_2)_3-CH(COOM)-CH_2COOM$, the polymer prepared by a hydrosilylation reaction of a polyalkylhydrogensiloxane and allyl succinic anhydride followed by hydrolysis of the anhydride groups. Preferably, the polyalkylhydrogensiloxane is polydimethylhydrogensiloxane and the polymer is terminated with trimethylsilyl groups.

The term "personal care or cosmetic composition" means any cosmetic product or preparation such as those described in the annex ("Illustrative list by category of cosmetic products") in European Directive n° 76/768/EEC dated 27$^{th}$ Jul. 1976, known as the Cosmetic Directive.

Said polyorganosiloxanes with the above formula (I) can be used in an amount of from about 0.1% to about 30%, preferably from about 3% to about 10% by weight, of said personal care compositions.

Except when otherwise indicated the proportions are shown in % by weight (in dry matter) based on the total weight of the cosmetic compositions.

The personal care or cosmetic compositions comprising said dicarboxy functionalized polyorganosiloxanes with the above formula (I) can be formulated in a wide variety of types of products for the skin and/or hair (or, more generally, keratin) such as mousses, gels (in particular hair dressing gels), conditioners, hair dressing formulations or to aid comb-through of hair, rinsing formulae, hand and body lotions, skin moisturising products, skin cleansing or disinfecting compositions, shower gels, toilet milks, cream foundations, make-up removal compositions, sun and ultraviolet radiation protection lotions, creams or gels, skin care creams, anti-age preparations, anti-acne preparations, local analgesics, mascaras, deodorants, anti-perspirants, lipsticks and other compositions of the same type.

Further, the present compositions, in particular skin cleansing, disinfecting or conditioning lotions and creams, can be incorporated into an insoluble substrate for application to the skin such as in the form of a treated wipe or a skin-contacting topsheet for a disposable product such as a baby diaper. Suitable water insoluble substrate materials and methods of manufacture are described in Riedel, "Nonwoven Bonding Methods and Materials," *Nonwoven World* (1987); *The Encyclopedia Americana*, vol. 11, pp. 147–153, vol. 21, pp. 376–383, and vol. 26, pp. 566–581 (1984); U.S. Pat. No. 3,485,786 to Evans, issued Dec. 23, 1969; U.S. Pat. No. 2,862,251, to Kalwarres; U.S. Pat. No. 3,025,585, Kalwarres; U.S. Pat. No. 4,891,227, to Thaman et al., issued Jan. 2, 1990; and U.S. Pat. No. 4,891,228 and U.S. Pat. No. 5,686,088 to Mitra et al., issued Nov. 11, 1997; U.S. Pat. No. 5,674,591; James et al; issued Oct. 7, 1997.

The use of dicarboxy functionalized polyorganosiloxanes having the above formula (I) permits to confer benefits such as an increase in shine, gloss or volume of hair, easier comb-through of hair, easier spreadability or slipperiness onto skin; it also permits a better persistence of active materials or benefits agents deposited onto the surface and consequently permits to maintain the activity of the composition deposited on the surface over time.

Said compositions can use a vehicle or a mixture of vehicles compatible with application to the hair and/or skin. Said vehicle can represent from about 0.5% to about 99.5% of the weight of said composition, preferably from about 5% to about 90%. The term "compatible with application to the skin and/or hair" as used here means that the vehicle neither damages nor exerts negative effects on the appearance of the hair and/or skin nor does it cause skin and/or eye and/or scalp irritation.

Said vehicles can be constituted by at least one solvent for dissolving or dispersing the ingredients used, such as water, $C_1$–$C_6$ alcohols, mixtures thereof, or other solvents such as acetone, hydrocarbons (such as isobutane, hexane, decane), halogenated hydrocarbons, esters (such as ethyl acetate, dibutyl phthalate), volatile silicones (such as cyclopentasiloxane, cyclohexasilonane) and mixtures thereof.

When the compositions are in the form of sprays, tonic lotions, gels, or mousses, the preferred solvents comprise water, ethanol, volatile silicones and mixtures thereof.

Mousses and aerosol sprays can also use a propellant (trichlorofluoromethane, dichlorodifluoromethane, difluoroethane, dimethylether, propane, n-butane or isobutane) which can generate products in the form of mousses or in the form of fine uniform sprays.

The vehicles can take a large number of forms, for example emulsions including water-in-oil, oil-in-water, and multiple emulsions. These emulsions cover a wide range of viscosities from about 100 to about 2000000 mPa.s.

Besides said dicarboxy functionalized polyorganosiloxanes with the above formula (I), these personal care or cosmetic compositions can also include at least about 0.5% by weight of at least one cosmetically acceptable ingredient.

Thus said compositions can comprise at least one surfactant; it can be anionic, non-ionic, cationic, zwitterionic or amphoteric in type (from about 1% to about 60%, preferably from about 5% to about 25%). Examples which can be cited are:

Anionic surfactants such as:
alkylester sulphonates with formula $R-CH(SO_3M)-COOR'$, where R represents a $C_8$–$C_{20}$ alkyl radical, preferably $C_{10}$–$C_{16}$, R' represents a $C_1$–$C_6$ alkyl radical, preferably $C_1$–$C_3$, and M represents an alkali cation (sodium, potassium, lithium), substituted or non substituted ammonium (methyl-, dimethyl-, trimethyl-, tetramethylammonium, dimethylpiperidinium) or derived from an alkanolamine (monoethanolamine, diethanolamine, triethanolamine). More particularly, methyl ester sulphonates where radical R is $C_{14}$–$C_{16}$ can be cited;
alkylsulphates with formula $ROSO_3M$, where R represents a $C_{10}$–$C_{24}$ alkyl or hydroxyalkyl radical, preferably $C_{12}$–$C_{20}$ and more particularly $C_{12}$–$C_{18}$, M represents a hydrogen atom or a cation with the same definition as above, and their oxyethylenated (OE) and/or propoxylenated (OP) derivatives with an average of 0.5 to 6 units, preferably 0.5 to 3 OE and/or OP units;
alkylamide sulphates with formula $RCONHR'OSO_3M$ where R represents a $C_{20}$–$C_{22}$ alkyl radical, preferably $C_6$–$C_{20}$, R' represents a $C_2$–$C_3$ alkyl radical, M represents a hydrogen atom or a cation with the same definition as above, and their oxyethylenated (OE) and/or propoxylenated (OP) derivatives with an average of 0.5 to 60 OE and/or OP units;
salts of saturated or unsaturated $C_8$–$C_{24}$ fatty acids, preferably $C_{14}$–$C_{20}$, $C_9$–$C_{20}$ alkylbenzenesulphonates, primary or secondary $C_8$–$C_{22}$ alkylsulphonates, alkylgycerolsulphonates, sulphonated polycarboxylic acids described in British patent GB-A-1 082 179, paraffin sulphonates, N-acyl-N-alkyltaurates, alkylphosphates, alkylisethionates, alkylsuccinamates, alkylsulphosuccinates, sulphosuccinate monoesters or diesters, N-acylsarcosinates, alkylglycoside sulphates, polyethoxycarboxylates, the cation being an alkali metal (sodium, potassium, lithium), a substituted or non substituted ammonium residue (methyl, dimethyl-, trimethyl-, tetramethylammonium, dimethylpiperidinium . . . ) or an alkanolamine derivative (monoethanolamine, diethanolamine, triethanolamine);

Non-ionic surfactants such as:
polyoxyalkylenated alkylphenols (polyethoxyethylenated, polyoxypropylenated, polyoxybutylenated) where the alkyl substituent is $C_6$–$C_{12}$ and containing 5 to 25 oxyalkylenated units; examples which can be cited are TRITON X-45, X-114, X-100 or X-102 sold by Rohm & Haas;
glucosamides, glucamides;
glycerolamides derived from N-alkylamines (U.S. Pat. No. 5,223,179 and FR-A-1 585 966);
polyoxyalkylenated aliphatic $C_8$–$C_{22}$ alcohols containing 1 to 25 oxyalkylenated units (oxyethylenated, oxypropylenated); examples which can be cited are TERGITOL 15-S-9, TERGITOL 24-L-6 NMW sold by Union Carbide Corp., NEODOL 45-9, NEODOL 23-65, NEODOL 45-7, NEODOL 45-4 sold by Shell Chemical, KYRO EOB sold by Procter & Gamble Co;
products resulting from condensing ethylene oxide with a hydrophobic compound resulting from condensing propylene oxide with propylene glycol, such as PLURONIC sold by BASF;
amine oxides such as $C_{10}$–$C_{18}$ alkyl dimethylamine oxides, $C_8$–$C_{22}$ alkoxy ethyldihydroxyethylamines;
alkylpolyglycosides described in U.S. Pat. No. 4,565,647 and their polyoxyalkylenated derivatives;
amides of $C_8$–$C_{20}$ fatty acids;
ethoxylated fatty acids;
ethoxylated amides, amines, amidoamines.

Amphoteric and zwitterionic surfactants such as
betaine type such as:
$R^1R^2R^{3+}NR^4C(O)O^-$ betaines;
$R^1R^2R^{3+}NR^4SO_3^-$ sulphobetaines;
$R^1C(O)$—NH $R^{2+}N(R^3R^4)R^5C(O)O^-$ amidoalkylbetaines
and $R^1C(O)$—NH $R^{2+}N(R^3R^4)R^5SO_3^-$ sulphobetaines in which formulae radical $R^1$ represents an alkyl or alkenyl radical containing 10 to 24 carbon atoms, $R^2$, $R^3$, $R^4$ and $R^5$, which may be identical or different, represent an alkyl or alkylene radical containing 1 to 4 carbon atoms;
the condensation products of fatty acids and protein hydrolysates;
cocoamphoacetates, cocoamphodiacetates, alkylamphopropionates or -dipropionates; amphoteric derivatives of alkylpolyamines such as AMPHIONIC XL® sold by RHODIA, AMPHOLAC 7T/X® and AMPHOLAC 7C/X® sold by AKZO NOBEL.

The composition of the invention can also comprise active materials and/or benefit agents, such as conditioning agents, moisturising agents, emollients, astringent or antiperspirant compounds, biocidal compounds, sunscreens or UV absorbers, pigments, perfumes, anti-aging agents, enzymes, proteins, and vitamins.

The conditioning agents which can be used are preferably selected from conditioners of synthetic origin, in particular the polyquaternium, such as the copolymer of N,N'-bis ((dimethylamino)-3 propyl)urea and oxy-1,1'bis(2-chloro) ethane or polyquaternium-2, the copolymer of diallyldimethyl ammonium chloride and acrylamide or polyquaternium-7, and cationic polysaccharide derivatives such as cocodimonium hydroxyethyl cellulose, guar hydroxypropyl trimonium chloride, hydroxypropyl guar hydroxypropyl trimonium chloride (JAGUAR C13S®, JAGUAR C 162® sold by RHODIA). They can represent up to about 1% of the composition.

The moisturizing agents which can be cited are glycerol, sorbitol, urea, collagen, gelatine, aloe vera, hyaluronic acid. They can represent up to about 10% of the composition.

The emollients which can be selected from alkylmonoglycerides, alkyldiglycerides, triglycerides such as oils extracted from plants and from vegetables (e.g., palm oil, coprah oil, cottonseed oil, soya bean oil, sunflower seed oil, olive oil, grapeseed oil, sesame oil, peanut oil, castor oil) or oils of animal origin (e.g., tallow, fish oils, etc.), derivatives of these oils such as hydrogenated oils, lanolin derivatives, mineral oils or paraffin oils, perhydrosqualane, squalene, diols such as 1,2-propanediol, 1,3-butanediol, cetyl alcohol, stearyl alcohol, oleic alcohol, polyethylene glycols or polypropylene glycols, fatty esters such as isopropyl palmitate, 2-ethylhexyl cocoate, myristyl myristate, esters of lactic acid, stearic acid, behenic acid, isostearic acid, silicone oils such as polydimethylsiloxanes, silicone copolyols (dimethicone copolyol, cetyldimethicone copolyol), diphenyldimethicones, phenyltrimethicones, dimethiconols, with viscosities in the range about 20 to about 10000 mPa.s. They can represent up to about 20% of the composition.

Astringent or antiperspirant compounds include organic or inorganic aluminium, zirconium, zinc salts or their mixed salts or mixtures thereof. These compounds have been described or cited in the literature, in particular in the review Cosmetics and Toiletries, April 1990, pages 35 to 39. Examples of these compounds are aluminium chloride, aluminium and/or zirconium hydrochlorides, aluminium chlorhydrex, aluminium-zirconium chlorhydrex glycine, aluminium sulphate, zinc sulphate, zirconium and aluminium chlorohydroglycinate, zirconium hydroxychloride, zirconium and aluminium lactate, aluminium and potassium sulphate, aluminium and sodium chlorohydroxylactate, aluminium hydrobromide, zinc sulphocarbonate, aluminium bromide, and zinc phenolsulphonate associated with aluminium sulphate. They can represent up to about 70% of the composition.

Biocidal compounds include chlorhexidine and its derivatives, nisin, triclosan and trichlorocarban. They can represent up to about 2% of the composition.

Organic molecules acting as UV filters, or mineral particles acting as a physical barrier to UV radiation are well known in the literature; for example, they have been described in the article in the review *Cosmetics and Toiletries*, vol 102, March 1987, p. 21 ff. Examples which can be cited are UV filters such as para amino benzoates and their derivatives, salicylates, cinnamates, benzophenones, benzylidene camphor, benzotriazoles and their derivatives and more generally filters cited in annex 7 of European Directive 76/768/EEC. These anti-UV filters can also be grafted onto a polymeric chain, in particular onto a polysiloxane chain. Mineral particles which can be cited include titanium oxide particles, zinc oxide particles or cerium oxide particles. These particles or nanoparticles of mineral oxides are optionally surface coated with polymers, organic molecules or other mineral compounds to improve their compatibility with organic phases and to reduce their surface reactivity, such as photocatalysis. They can represent up to about 25% of the composition.

Organic pigments are generally aromatic in nature such as azo, indigoid, triphenylmethane, anthraquinone, xanthine and are taken up in denominations D&C and FD&C. Inorganic pigments are generally metal oxides or metal insoluble metal salts of colouring agent additives; they include titanium dioxide codified in the Color Index CI 77891, black, red and brown iron oxides (CI 77499, CI 77492 and CI 77491), manganese violet (CI 77742), ultramarine violet or blue (CI 77007), chromium oxide (CI 77288). They can represent from about 5 to 50% of the composition.

Flavor, essential oils, perfumes can include benzaldehyde, caraway oil, cardamon oil, cinnamon oil, ethylvanilin, eucalyptus globulus oil, glutamic acid, clove oil, orange oil, peppermint oil, thymol, phenethyl alcohol or their mixtures. They can represent up to about 3% of the composition.

Anti-aging agents can include carrot extract, Ceramide 33, hydrolyzed serum protein. They can represent up to about 1% of the composition.

Enzymes can include lipase, papain, soy protein and coenzymes such as ubiquinone Q10. They can represent up to about 1% of the cosmetic composition.

Proteins can include collagen, collagen derivatives, keratin. They can represent up to about 3% of the composition.

Retinol, retinyl palmitate, tocopherol, tocopherol acetate, menadione, ascorbic acid and ascorbyl palmitate are examples of vitamins that can be included in the present compositions. They can represent up to about 0.5% of the composition.

Said personal care or cosmetic compositions can also contain other additives usually present in cosmetic compositions. It can contain:
  non hydrosoluble and non volatile polyorganosiloxane oils, gums or resins, particularly diphenylmethicone gums sold by Rhodia, preferably polydimethylsiloxanes with a viscosity of at least about 60000 mPa.s at 25° C., more preferably those with a viscosity of more than about 2000000 mPa.s at 25° C., such as Mirasil DM 500000® sold by Rhodia. They can represent up to about 10% of the composition.
  polymers with film-forming properties, which can be used as fixative resins. Preferably, the film-forming polymers are polyvinylpyrrolidone (PVP) in type, or copolymers of polyvinylpyrrolidone and methyl methacrylate, polyvinylpyrrolidone and vinyl acetate (VA) copolymers, ethylene glycol polyterephthalate/polyethylene glycol copolymers, ethylene glycol polyterephthalate/polyethylene glycol/sodium polyisophthalate sulphonate copolymers, and mixtures thereof. They can represent from about 0.01 to about 10%, preferably from about 0.5 to about 5% of the composition.
  plasticizers, such as adipates, phtalates, isophtalates, azelate, stearates, silicone copolyols, glycols, castor oil or mixture thereof. They can represent from about 0.1 to about 5% of the composition.
  sequestring agents such as citrate ions. They can represent up to about 2% of the composition.
  hydrosoluble or hydrodispersible polymers able to reduce the irritation or aggravation of cutaneous tissue, such as collagen or certain non allergising derivatives of animal or vegetable proteins (for example wheat germ protein hydrolysates), natural hydrocolloids (guar gum, carouba gum, tara gum) or from fermentation methods and derivatives of these polycarbohydrates such as modified celluloses (for example hydroxyethylcellulose, carboxymethylcellulose), guar derivatives or carouba derivatives such as their cationic derivatives or their non ionic derivatives (for example hydroxypropylguar), anionic derivatives (carboxymethylguar and carboxymethyl hydroxypropylguar). They can represent up to about 5% of the composition.
  thickening, gelling or solidifying agents such as lithium, sodium, potassium, aluminium zirconium, cerium salts of stearic, hydroxystearic, behenic, montanic acids, esters of $C_{14}$–$C_{30}$ carboxylic or hydroxycarboxylic acids and the glycol, polyglycol, glycerol or polyglycerol of $C_2$–$C_{30}$ aliphatic alcohols, $C_{14}$–$C_{30}$ polyethylene glycol or polypropylene glycol ethers, $C_{14}$–$C_{30}$ aliphatic alcohols, xanthan gum, silicone waxes such as behenic ester dimethicone. They can represent up to about 2% of the composition.
  powders such as bismuth oxychloride, mica and titanium mica, silica which may be functionalised, synthetic polymers such as Teflon, polyacrylates, polyethylenes or nylon, alumina silicate, bentonites, cellulose, magnesium derivatives such as the aluminosilicate, oxide, carbonate or hydroxide, montmorillonites, talc, zinc stearate, titanium oxide, cerium oxide, or mixtures thereof. They can represent up to about 50% of the composition.
  waxes such as silicone waxes (behenic ester dimethicone), ceresin, ozokerite, carnauba wax, candilla wax or mixtures thereof.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope. All percentages used herein are by weight of the composition unless otherwise indicated.

Example 1

Preparation of a Dicarboxy Functionalized Polydimethylsiloxane Having Pendant —(CH$_2$)$_3$—CH(COOH)—CH$_2$COOH Groups 93.7 g (i.e., 0.67 mol) of allyl succinic anhydride, 52 g of toluene and 1.01 g of a Kardtedt catalyst solution (0.1% of Pt in hexamethyldisiloxane) are added into a 500 ml reactor. The reaction mass is heated at 90° C.; 120 g (i.e., 0.45 mol of SiH) of a polydimethylhydrogenosiloxane having the formula

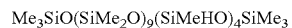

Me$_3$SiO(SiMe$_2$O)$_9$(SiMeHO)$_4$SiMe$_3$ and containing 3.75 mol of SiH/kg, are added over 3 hours. The SiH amount (determined by gazometry) transformed at the end of the addition is of 96.1%; it is of 100% 2 hours after the end of the addition. The volatiles are eliminated by evaporation under vacuum (3 mbar) over 10 hours at 150° C. 15 g of demineralized water are then added in order to hydrolyze the succinic anhydride functions. The hydrolysis reaction is followed by infra-red analysis (acid band at 1714 cm$^{-1}$, anhydride band at 1863 and 1782 cm$^{-1}$). When the hydrolysis reaction is complete (48 hours), 100 g of toluene are added in order to azeotropically eliminate water. 133.5 g (corresponding to a yield of 82%) of a viscous oil are recovered.

NMR analysis confirmed the following general structure of the product obtained:

$$Me_3SiO(SiMe_2O)_9(SiMeAO)_4SiMe_3$$

in which A represents —$(CH_2)_3$—CH(COOH)—$CH_2COOH$.

Example 2

Preparation of a Dicarboxy Functionalized Polydimethylsiloxane Having Pendant —$(CH_2)_3$—CH(COOH)—$CH_2COOH$ Groups 49.8 g (i.e., 0.36 mol) of allyl succinic anhydride, 44 g of toluene and 1.139 g of a Kardtedt catalyst solution (0.1% of Pt in hexamethyldisiloxane) are added into a 500 ml reactor. The reaction mass is heated at 90° C.; 150.3 g (i.e., 0.266 mol of SiH) of a polydimethylhydrogenosiloxane having the formula $$Me_3SiO(SiMe_2O)_{100}(SiMeHO)_{15}SiMe_3$$

and containing 1.77 mol of SiH/kg, are added over 1 hour. The SiH amount (determined by gazometry) transformed at the end of the addition is of 86%; it is of 100% 16 hours after the end of the addition. The volatiles are eliminated by evaporation under vacuum (6 mbar) over 10 hours at 150° C. 101 g of toluene are added; the reaction mass is filtered. 6.7 g of demineralized water are then added in order to hydrolyzed the succinic anhydride functions. The hydrolysis reaction is followed by infra-red analysis (acid band at 1714 cm$^{-1}$, anhydride band at 1866 and 1788 cm$^{-1}$). When the hydrolysis reaction is complete (6 days), water is azeotropically eliminated. 146.3 g (corresponding to a yield of 80%) of a viscous oil are recovered.

NMR analysis confirmed the following general structure of the product obtained:

$$Me_3SiO(SiMe_2O)_{100}(SiMeAO)_{15}SiMe_3$$

in which A represents —$(CH_2)_3$—CH(COOH)—$CH_2COOH$

Example 3

Anti-perspirant/deodorant

| INGREDIENTS | % BY WEIGHT |
|---|---|
| 1. Cyclomethicone | 7 |
| 2. Dimethicone copolyol | 5 |
| 3. Product from Example 1 or 2 | 7 |
| 4. Aluminium hydrochloride | 50 |
| 5. Propylene glycol | 15 |
| 6. Water | 16 |

Example 4

Cream Foundation

| INGREDIENTS | % BY WEIGHT |
|---|---|
| 1. Behenic ester dimethicone | 2.0 |
| 2. Product from Example 1 or 2 | 3.0 |
| 3. PEG-stearate (polyethylene glycol stearate) | 2.5 |
| 4. Isopropyl myristate | 3.0 |
| 5. Stearic acid | 5.0 |
| 6. Talc | 12.0 |
| 7. Titanium oxide | 5.0 |
| 8. Red iron oxide | 0.5 |
| 9. Preservative | 0.2 |
| 10. Fragrance | 0.2 |
| 11. Deionised water | qs 100 |

Example 5

Solar Lotion

| INGREDIENTS | % BY WEIGHT |
|---|---|
| Product from Example 1 or 2 | 10 |
| Cyclomethicone | 10 |
| Parsol MCX | 5 |
| Isopropyl myristate | 5 |
| Oleth-25 | 2 |
| Ceteth-20 | 1 |
| Potassium lauryl phosphate | 2 |
| Glycerol | 3 |
| Deionised water | 62 |

Example 6

Moisturizing Anti-transfer Lipstick

| INGREDIENTS | % BY WEIGHT |
|---|---|
| 1. Behenic ester dimethicone | 15 |
| 2. Product from Example 1 or 2 | 10 |
| 3. Carnauba wax | 2 |
| 4. Ceresin wax | 4 |
| 5. Candellila wax | 5 |
| 6. Microcrystalline wax | 2 |
| 7. Beeswax | 5 |
| 8. Lanolin | 4 |
| 9. Castor oil | 20 |
| 10. Hexadecyl alcohol | 20 |
| 11. Glycerol | 3 |
| 12. Glycerol monostearate | 2 |
| 13. Titanium oxide | 2 |
| 14. Red#202 pigment | 2 |
| 15. Red#4A1 lake pigment | 3 |
| 16. Red#204 pigment | 1 |
| 17. Antioxidant | q.s. |
| 18. Fragrance | q.s. |

Example 7

Make-up Removing Milk

| INGREDIENTS | INCI NAME | % BY WEIGHT |
|---|---|---|
| PHASE A | | |
| Paramul J | Cetearyl alcohol and ceteareth-20 | 2.00 |
| Dermol DISD | Diisostearyl dimer dilinoleate | 4.00 |
| Waglinol 6016 | Isopropyl palmitate | 7.00 |
| Camelia oil | Camelia kissi oil | 4.00 |
| Alcohol 260 | Ethanol | 1.00 |
| PHASE B | | |
| Distilled water | Aqua | 73.70 |
| Rhodicare S | Xanthan gum | 1.00 |
| PHASE C | | |
| Miranol C2M conc NP | DiNa cocoamphodiacetate | 2.00 |
| PHASE D | | |
| Product from Expl 1 or 2 | | 5.00 |
| PHASE E | | |
| Fragrance FBF 0239 | Fragrance | 0.30 |
| 50% citric acid | Citric Acid | q.s. to pH 6.2 |

Example 8

After-sun Cream

| INGREDIENTS | INCI NAME | % BY WEIGHT |
|---|---|---|
| PHASE A | | |
| Product from Ex. 1 or 2 | | 5.00 |
| MIRASIL C-DPDM | Cyclomethicone (and) diphenyldimethicone | 5.0 |
| Octyl cocoate | Octyl cocoate | 7.0 |
| Jojoba oil | Jojoba (Buxus Chinensis) oil | 2.0 |
| Grapeseed oil | Grape (Vitis Vinifera) seed oil | 1.0 |
| PHASE B | | |
| TEFOSE 63 | PEG-6 (and) PEG-32 (and) glycol stearate | 10.0 |
| Allantoin | Allantoin | 0.5 |
| Deionised water | Aqua | q.s. 100 |
| PHASE C | | |
| Preservative | Preservative | q.s. |
| PHASE D | | |
| Fragrance | Fragrance | q.s. |

Example 9

Sun Oil

| INGREDIENTS | INCI NAME | % BY WEIGHT |
|---|---|---|
| Cyclomethicone | Cyclomethicone | 27.0 |
| Isopropyl palmitate | Isopropyl palmitate | 25.0 |
| Diisopropyl adipate | Diisopropyl adipate | 25.0 |
| Product from Example 1 or 2 | | 5.0 |
| MIRASIL C-DPDM | Cyclomethicone (and) Diphenyldimethicone | 15.0 |
| Benzophenone-3 | Benzophenone-3 | 3.0 |
| Colouring agent | Dye | q.s. |

Example 10

Day Cream

| INGREDIENTS | CTFA NAME | % BY WEIGHT |
|---|---|---|
| PHASE A | | |
| Mineral oil | Mineral oil | 5.0 |
| Miglyol 812 N | Caprylic/capric triglyceride | 5.0 |
| Isopropyl myristate | Isopropyl myristate | 3.0 |
| Sunflower seed oil | Sunflower seed oil | 4.0 |
| Product from Exple 1 or 2 | | 0.5 |
| Lorol C18 | Stearyl alcohol | 1.0 |
| Alpha-Tocopherolacetate | Tocopheryl acetate | 2.0 |
| PHASE B | | |
| Hydrogenated palm oil sucroglyceride | Hydrogenated palm oil sucroglyceride | 5.0 |
| Glycerin | Glycerin | 3.0 |
| Preservative | Preservative | q.s. |
| Deionised water | Aqua | q.s. 100 |
| RHODICARE S | Xanthan gum | 0.2 |

Example 11

Cream Base

| INGREDIENTS | INCI NAME | % BY WEIGHT |
|---|---|---|
| PHASE A | | |
| Mirasil DM300 | Dimethicone | 15.0 |
| Product from Example 1 | | 5.0 |
| PHASE B | | |
| Rhodicare S | Xanthan gum | 0.15 |
| Arlatone 2121 | Sorbitan stearate (and) sucrose cocoate | 5.5 |
| Glycerin | Glycerin | 4.0 |
| Preservative | Preservative | q.s. |
| Water | Aqua | q.s. 100 |

Example 12

Night Cream

| INGREDIENTS | CTFA NAME | % BY WEIGHT |
|---|---|---|
| PHASE A | | |
| Mineral oil | Mineral oil | 15.0 |
| Arlamol HD | Isohexadecane | 10.0 |
| Miglyol 812 N | Caprylic/capric triglyceride | 5.0 |
| Wheat Germ Oil | Wheat germ oil | 3.0 |

-continued

| INGREDIENTS | CTFA NAME | % BY WEIGHT |
|---|---|---|
| Product from Ex. 1 or 2 | | 0.5 |
| Arlacel 60 | Sorbitan stearate | 2.0 |
| Lorol C18 | Stearyl alcohol | 0.5 |
| α-tocopherol acetate | Tocopheryl acetate | 1.0 |
| PHASE B | | |
| Hydrogenated palm oil Sucroglyceride | Hydrogenated palm oil Sucroglyceride | 5.0 |
| Glycerin | Glycerin | 4.0 |
| Preservative | Preservative | q.s. |
| RHODICARE S | Xanthan gum | 0.3 |
| Water | Aqua | q.s. 100 |

Example 13

Solar Emulsion (Oil-in-Water) with SPF of 10

| INGREDIENTS | CTFA NAME | % BY WEIGHT |
|---|---|---|
| PHASE A | | |
| Arlatone 985 | POE-5-stearyl stearate | 4.0 |
| Brij 721 | Steareth-21 | 2.0 |
| Parsol MCX | Octyl methoxycinnamate | 5.0 |
| Product from Example 1 or 2 | | 4.0 |
| DUB DNPG | Neopentyl diheptanoate | 4.0 |
| Dermol M5 | Caprylic/capric triglycerides | 3.0 |
| Grapeseed oil | Grape (Vitis Vinifera) seed oil | 3.0 |
| MIRASIL WAX B | Behenic ester dimethicone | 1.0 |
| Oxynex 2004 | BHT (and) glyceryl stearate (and) glyceryl oleate (and) ascorbyl palmitate (and) citric acid (and) propylene glycol | 0.1 |
| PHASE B | | |
| Deionised water | Aqua | qsp 100 |
| Atlas G2330 | Sorbeth-30 | 4.0 |
| Preservative | — | qs |
| Fragrance | Fragrance | qs |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Personal care composition for the cleaning or the treatment of hair and/or skin comprising at least one dicarboxy functionalized polyorganosiloxane of formula (I)

$$X(R^4R^5SiO)_p(R^6ASiO)_qY \qquad (I)$$

wherein
X represents a triorganosiloxyl end group of formula $R^1R^2R^3SiO—$, or a Z end group wherein Z represents —OH;

Y represents a triorganasilyl end group of formula —SiR³R²R¹ or a W end group wherein W represents —H;

$R^1$ to $R^6$, which may be identical or different, each represents a linear or branched C1–C8 alkyl or phenyl radical;

A represents a dicarboxy acid radical of formula

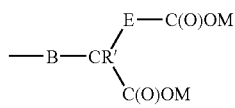

wherein
B represents an alkylene residue having from 2 to 30 carbon atoms, optionally substituted by one or more alkyl radicals having from 1 to 30 carbon atoms, R' represents a hydrogen atom or an alkyl radical having from 1 to 30 carbon atoms, and E is nil or is an alkylene residue having from 1 to 5 carbon atoms, optionally substituted by one or more alkyl radicals having from 1 to 30 carbon atoms; and M is H or a cation selected from the group consisting of alkali metal, alkaline earth metal, and substituted or non substituted aminonium, piperidinium or alkanolamine;

p is an avenge value ranging from 0 to 1000;

q is an average value ranging from 1 to 100; and the p/q ratio is from 1/1 to 10/1; and the ratio of the number of Z and W end groups to the total number of X and Y end groups is from 0/100 to 75/100;

said personal care composition is in a form selected from the group consisting of a hair dressing, a conditioner, a formulation to aid comb-through of hair, a hair rinsing formulation, a hand and body lotion, a skin cleanser, a skin disinfectant, a shower gel, a toilet milk, a cream foundation, a make-up removal composition, a sun and ultra-violet radiation protection lotion, cream or gel, a skin care cream, an anti-age preparation, an anti-acne preparation, a mascara, a deodorant, an anti-perspirant, or a lipstick;

wherein said personal care composition comprises at least one cosmetically acceptable ingredient.

2. Personal care formulation according to claim 1, in which A represents a —(CH₂)₃—CH(COOM)—CH₂COOM group.

3. Personal care composition according to claim 1, in which said dicarboxy franctionalized polyorganosiloxane of fonnula (I) represents from about 0.1% to about 30% by weight of said personal care composition.

4. Personal care composition according to claim 1, which further comprises at least about 0.5% by weight, relative to the total weight of said personal care composition, of at least one vchicle and/or said cosmetically acceptable ingredient.

5. Personal care composition according to claim 4, which comprises at least one conditioning agent, moisturizing agent, emollient, astrigent or antiperspirant compound, blocidal compound, sunscreen or UV absorber, pigment, perfume, anti-aging agent, enzyme, protein, vitamin or a mixture thereof.

* * * * *